(12) United States Patent
Kantro (10) Patent No.: US 11,417,425 B2
(45) Date of Patent: Aug. 16, 2022

(54) SYSTEM AND METHOD FOR MANAGEMENT OF DIABETIC FOOT CARE PATIENTS

(71) Applicant: Scott Kantro, Pound Ridge, NY (US)

(72) Inventor: Scott Kantro, Pound Ridge, NY (US)

( * ) Notice: Subject to any disclaimer, the term of this patent is extended or adjusted under 35 U.S.C. 154(b) by 174 days.

(21) Appl. No.: 16/825,555

(22) Filed: Mar. 20, 2020

(65) Prior Publication Data
US 2021/0295982 A1 Sep. 23, 2021

(51) Int. Cl.
| | |
|---|---|
| *G16H 40/20* | (2018.01) |
| *G16H 10/20* | (2018.01) |
| *G16H 10/60* | (2018.01) |
| *G06Q 10/10* | (2012.01) |
| *G16H 40/67* | (2018.01) |
| *G08B 21/02* | (2006.01) |
| *A61B 5/00* | (2006.01) |
| *A61B 5/01* | (2006.01) |
| *A61B 5/103* | (2006.01) |
| *A61B 5/107* | (2006.01) |

(Continued)

(52) U.S. Cl.
CPC ............ *G16H 40/20* (2018.01); *A61B 5/01* (2013.01); *A61B 5/1036* (2013.01); *A61B 5/1074* (2013.01); *A61B 5/443* (2013.01); *A61B 5/447* (2013.01); *A61B 5/4827* (2013.01); *A61B 5/7275* (2013.01); *G06Q 10/06316* (2013.01); *G06Q 10/10* (2013.01); *G08B 21/02* (2013.01); *G16H 10/20* (2018.01); *G16H 10/60* (2018.01); *G16H 15/00* (2018.01); *G16H 40/67* (2018.01); *G16H 50/20* (2018.01); *G16H 50/30* (2018.01); *G16H 50/70* (2018.01); *G16H 70/20* (2018.01)

(58) Field of Classification Search
USPC ......................................................... 705/2–3
See application file for complete search history.

(56) References Cited

U.S. PATENT DOCUMENTS

| | | | |
|---|---|---|---|
| 10,993,654 B2 * | 5/2021 | Najafi | ...................... A61B 5/01 |
| 2004/0049408 A1 * | 3/2004 | Voss | ....................... G16H 20/60 |
| | | | 705/2 |

(Continued)

OTHER PUBLICATIONS

Cruz-Torio, Leslie, "Urgent Care Nurse Data Capture: Impact on Diabetes Outcomes", University of San Diego, Hanh School of Nursing and Health Science, pp. 1-201, 2015 (Year: 2015).*

*Primary Examiner* — Amber A Misiaszek
(74) *Attorney, Agent, or Firm* — Sofer & Haroun, LLP (57) ABSTRACT

The present arrangement provides a system for managing diabetic foot care patients that include a communication interface for transmitting diagnostic forms to a doctor device and receiving input from the doctor device. A processor manages the transmissions and received input and a database storing the diagnostic forms and the received input, as well as pre-stored risk assessment guidelines. The system is configured to transmit the diagnostic forms to a doctor device for guiding a comprehensive foot exam, and further, to accept doctor input including at least a plurality of foot examination details and a risk pool assessment. The system compares at least a plurality of foot examination details against the pre-stored risk assessment guidelines and confirms or reject the risk pool assessment input by the doctor if the risk pool assessment is or is not congruent with requirements contained in the pre-stored risk assessment guidelines.

6 Claims, 11 Drawing Sheets

(51) Int. Cl.
*G16H 70/20* (2018.01)
*G06Q 10/06* (2012.01)
*G16H 50/30* (2018.01)
*G16H 50/70* (2018.01)
*G16H 50/20* (2018.01)
*G16H 15/00* (2018.01)

(56) References Cited

U.S. PATENT DOCUMENTS

2010/0280849 A1* 11/2010 Hinkes .................. G16H 50/30
707/769
2018/0220954 A1* 8/2018 Burns .................. A61B 5/0531

* cited by examiner

| Conducting a CDFE  | |
|---|---|
| CDFE Workflow | |
| Step 1 | Clinical Update Form |
| Step 2 | Patient Info and Authorization for Release of Information |
| Step 3 | Dermatological - DermaStat, IRStat |
| Step 4 | Left Foot Assessment |
| Step 5 | Right Foot Assesment |
| Step 6 | Orthopedic |
| Step 7 | Foot Measurements |
| Step 8 | Neurological |
| Step 9 | Vascular |
| Step 10 | Risk Stratification, Education and Counseling |
| Step 11 | Examiner signature |
| Step 12 | Take photos and upload Pressure stat, Risk stratification and Footcare Tip images |
| Step 13 | Patient Survey |
| Step 14 | Prescription for therapeutic footwear and insoles (if eligible) |
| Step 15 | Examiner signature for prescription |
| Step 16 | TempStat RX (if eligible) |
| Step 17 | Dispensing (if applicable) |
| Step 18 | Call to follow up with patient (two weeks after shoes dispense) |

In the pop-up window, select the desired contents of the Audit Package.
Then click on Pre or Post-Payment

SYSTEM AND METHOD FOR MANAGEMENT OF DIABETIC FOOT CARE PATIENTS

BACKGROUND

Field of the Invention

This application relates to medical patient management. More particularly, this application relates to medical patient management with a focus on foot care and/or diabetic foot care.

Description of Related Art

Diabetes is a disease that affects a large portion of the U.S. and world population. As a result, costs associated with treating diabetes is in excess of 100 billion dollars per/year, a large portion of which is covered by various insurances and/or Medicare/Medicaid.

Regarding the podiatric aspect of diabetes, one effect of diabetes is neuropathy which causes a loss of feeling/sensation in the patients' extremities. One common effect of neuropathy in diabetic patients is foot ulceration. Essentially, patients develop foot ulcerations, and absent any feeling in the extremity, and if the ulcer is left untreated, even undetected, it could result in serious issues for the patient, up to and including amputation. For example, up to 25% of individuals with diabetes will develop a foot ulcer during their lifetime. Foot ulcers and infections are a very common reason for hospital admission of individuals with diabetes.

Such ulcers are a significant portion of the overall health care costs associated with diabetic treatment. As noted above, in more extreme cases, they result in amputations, which are too common in diabetic patients. These major limb amputations even further increase the costs of diabetic health care. (Rogers et al.—The Right to Bear Legs—An Amendment to Healthcare: How Preventing Amputations Can Save Billions for the US Health-care System—Journal of the American Podiatric Medical Association●Vol 98●No 2●March/April 2008)

One way to manage such issues is to perform a comprehensive diabetic foot exam and to place patients in a risk pool according to the patients' history in combination with the Exam results.

There are known stratification classifications to handle the different risk pools. These classifications then would indicate to a treating physician the likelihood of diabetic foot issues (e.g. ulceration etc. . . . ) occurring in the future, and also include guidelines for the frequency of follow-up appointments.

The following Table 1 is an exemplary chart for stratification/identification of patients in different risk pools.

TABLE 1

Table. Suggested frequency for follow-up evaluation

| Category | Risk profile | Evaluation frequency |
|---|---|---|
| 0 | Normal | Annual |
| 1 | Peripheral neuropathy | Semiannual |
| 2 | Neuropathy with deformity and/or PAD | Quarterly |
| 3 | Previous ulcer or amputation | Monthly or quarterly |

PAD, Peripheral arterial disease.

(Hingorani et al.—The management of diabetic foot: A clinical practice guideline by the Society for Vascular Surgery in collaboration with the American Podiatric Medical Association and the Society for Vascular Medicine—JOURNAL OF VASCULAR SURGERY Volume 63, Number 2S)

However, despite such classifications there are still a number of drawbacks associated with the prior art.

As a first point, even though doctors conduct a diabetic foot assessment to arrive at their diagnosis/classification, some doctors can accidentally ascribe an incorrect category to a patient, either through an oversight or simply a transcription error. For example, in a case where a patient has had a prior ulcer, they should be classified in class 3 but doctors may, for example in their internal scheduling and document management service, accidentally list them as a 0 or 1. Such a misdiagnosis could result in too infrequent of follow up visitations for that high risk patient. The opposite could occur as well, where a patient with little or no significant risk factors could be classified in class 3, but really should in in class 0 or 1. This could result in unnecessary extra visits and/or issues with insurance reimbursements.

Aside from the above issues, some diabetic foot patients are eligible for specialized footwear and/or inserts to prevent ulceration. Special shoes and insoles are a mainstay of ulcer prevention in high-risk patients with diabetes. In the United States, the Therapeutic Shoe Bill has provided shoes and insoles for high-risk Medicare beneficiaries with diabetes since 1993. Unfortunately, these services are dramatically underused. Only 7% to 16% of high-risk patients are prescribed therapeutic shoes and insoles.

Several studies have shown a significant reduction in foot ulcers in patients that receive therapeutic shoes compared with shoes patients would normally select themselves. There are a variety of insole materials and material combinations and different accommodations that can be built into the insole. Likewise, the type of shoe and outer sole accommodations are numerous.

Most of the decisions for protective shoes and insoles are left to technicians that have little working knowledge of the medical literature. When patients re-ulcerate they do not return to the pedorthist or shoe maker for care, so these providers have no follow-up to determine if their approach is effective. (Lawrence et al. Preventing the First or Recurrent Ulcers Lawrence—Med Clin N Am 97 (2013) 807-820)

One issue regarding these prescriptions is that to qualify there are list of qualifying "clinical risk indicators" used by Medicare to ensure that a patient qualifies for therapeutic footwear and insoles. However, the clinical risk indicators for therapeutic footwear and insoles are not a 100% overlap with the above described general classification/risk pool criteria. In other words, even after a physician performs a diabetic foot assessment, the classification alone is not always a qualification for footwear. Patients classified in higher risk classes like class 2 or class 3 are always eligible, but classes 0 and 1 may or may not be eligible.

In some cases, risk factors that don't automatically move a patient into a high-risk category may still be enough to qualify for Medicare and other insurance covered footwear/insoles based on the presence of certain clinical risk indicators. Although there is obviously overlap, the criteria and qualifications for payor reimbursement are different. Currently, a physician would have to independently confirm qualification under the clinical risk indicators to confirm that they are eligible for therapeutic footwear and insoles. This is at least one cause of the above described underutilization of such items.

Separately, assuming a physician were to prescribe and submit the necessary paperwork for therapeutic footwear and insoles for a diabetic foot patient, they would still need to procure approval from the physician managing the diabetes, and they would furthermore need, on occasion account for correct prescriptions in an insurance/Medicare audit which, with present systems is a complex and disorganized process.

Even assuming correct classification and treatment are prescribed, and assuming the correct therapeutic footwear and insoles are approved and prescribed, there is still a need to improve monitoring across all class of risk pools. It is known that at home monitoring can improve/reduce the instances of ulcerations leading to life-threatening complications and amputations.

For example, daily thermography has been demonstrated to significantly reduce both initial and re-ulceration rates. With daily thermography, patients' plantar foot skin temperature gradients are measured by standing on a thermography scale or using a specialized cutaneous temperature probe. (Barshes et al.—The system of care for the diabetic foot: objectives, outcomes, and opportunities—Diabetic Foot & Ankle 2013, 4: 21847)

However, while there may be several iterations for monitoring of the diabetic foot, none are part of a multi-modal program that provides line of sight to the podiatrist about the care and management of an entire stratified population of people with diabetes, and which also transmits information to the doctors for appropriate recordation of the results and/or follow up modifications.

OBJECTS AND SUMMARY

The present arrangement is directed to overcoming the prior art issues and to provide a comprehensive diabetic foot care patient management system. The present system not only allows doctors to classify their patients in a risk pool according to industry standards, but it also includes monitoring and checking of the classifications for obvious errors. Moreover, the system allows for the information and diagnosis of the patient classifications to be simultaneously run against a separate clinical risk indicator checklist to see if the same patient also qualifies for therapeutic footwear and insoles under the relevant Medicare guidelines.

The present arrangement tracks such assessment data and also generates required forms to include necessary prescription forms as well as secondary audit forms when needed.

In another embodiment the patient tracking system also couples with an external home monitoring application, where patients' home monitoring results can be easily integrated into the patients' files, generating alerts to the patients and/or physicians to adjust their follow-up appointment times in the cases of abnormal home results indicating a potential issue.

To this end the present arrangement provides a system for managing diabetic foot care patients that include a communication interface for transmitting diagnostic forms to a doctor device and receiving input from the doctor device. A processor manages the transmissions and received input and a database storing the diagnostic forms and the received input, as well as pre-stored risk assessment guidelines. The system is configured to transmit the diagnostic forms to a doctor device for guiding a comprehensive foot exam, and further, to accept doctor input including at least a plurality of foot examination details and a risk pool assessment. The system compares at least a plurality of foot examination details against the pre-stored risk assessment guidelines and confirms or reject the risk pool assessment input by the doctor if the risk pool assessment is or is not congruent with requirements contained in the pre-stored risk assessment guidelines.

BRIEF DESCRIPTION OF DRAWINGS

The present invention can be best understood through the following description and accompanying drawing, wherein.

DETAILED DESCRIPTION

Figure 1:
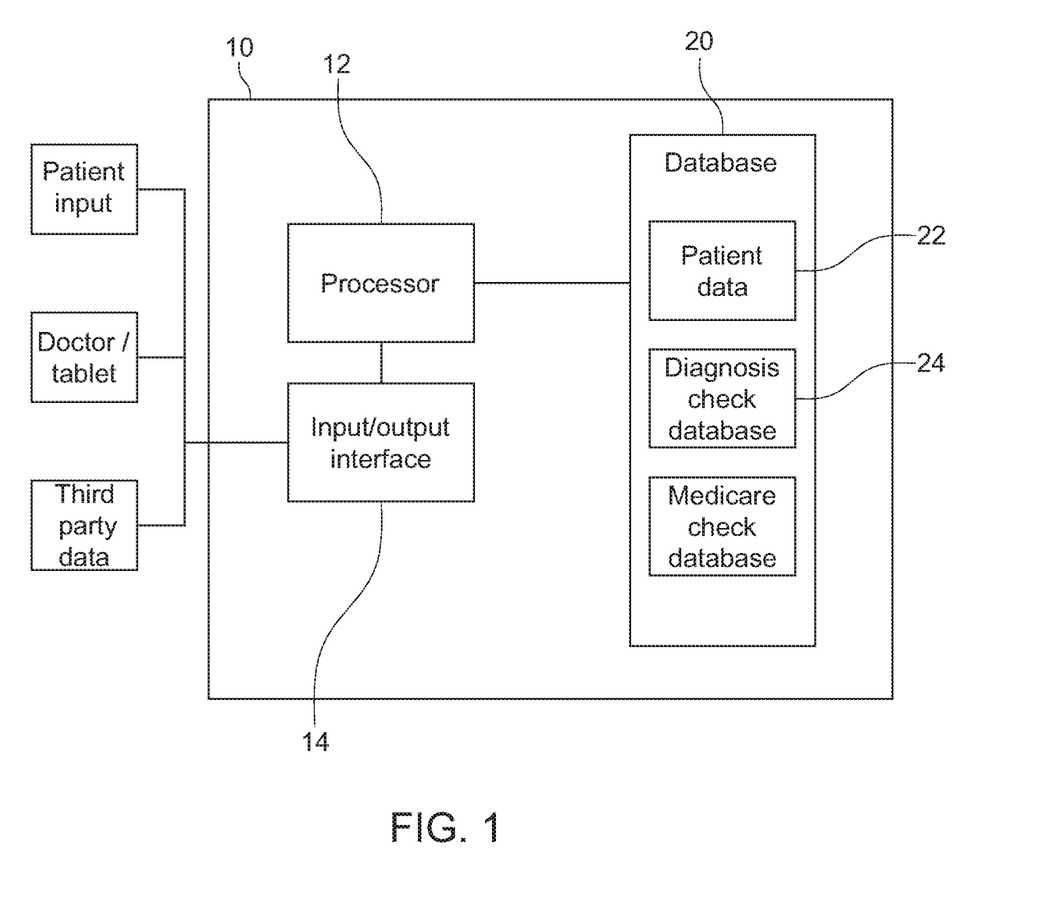
FIG. 1 is a system architecture overview, in accordance with one embodiment.

In one embodiment of the present arrangement, FIG. 1 shows an exemplary system to implement the features and steps of the present invention. A management system 10 may include a processor 12, and input/output interface 14 for connecting with doctors, patients and third-party data providers. Finally, system 10 includes a database 20 that includes directories for at least patient data 22, diabetic foot care analysis data 24, and Medicare data 26, all of which are explained in more detail below. It is understood that that such modules are shown in system diagram 10 as being co-located, but it is understood that such components may be implemented within a software on a computer(s) within a doctor's office, implemented as a cloud system for remote access or combinations thereof. The modules are shown in FIG. 1 for their exemplary functions only.

Figure 2:
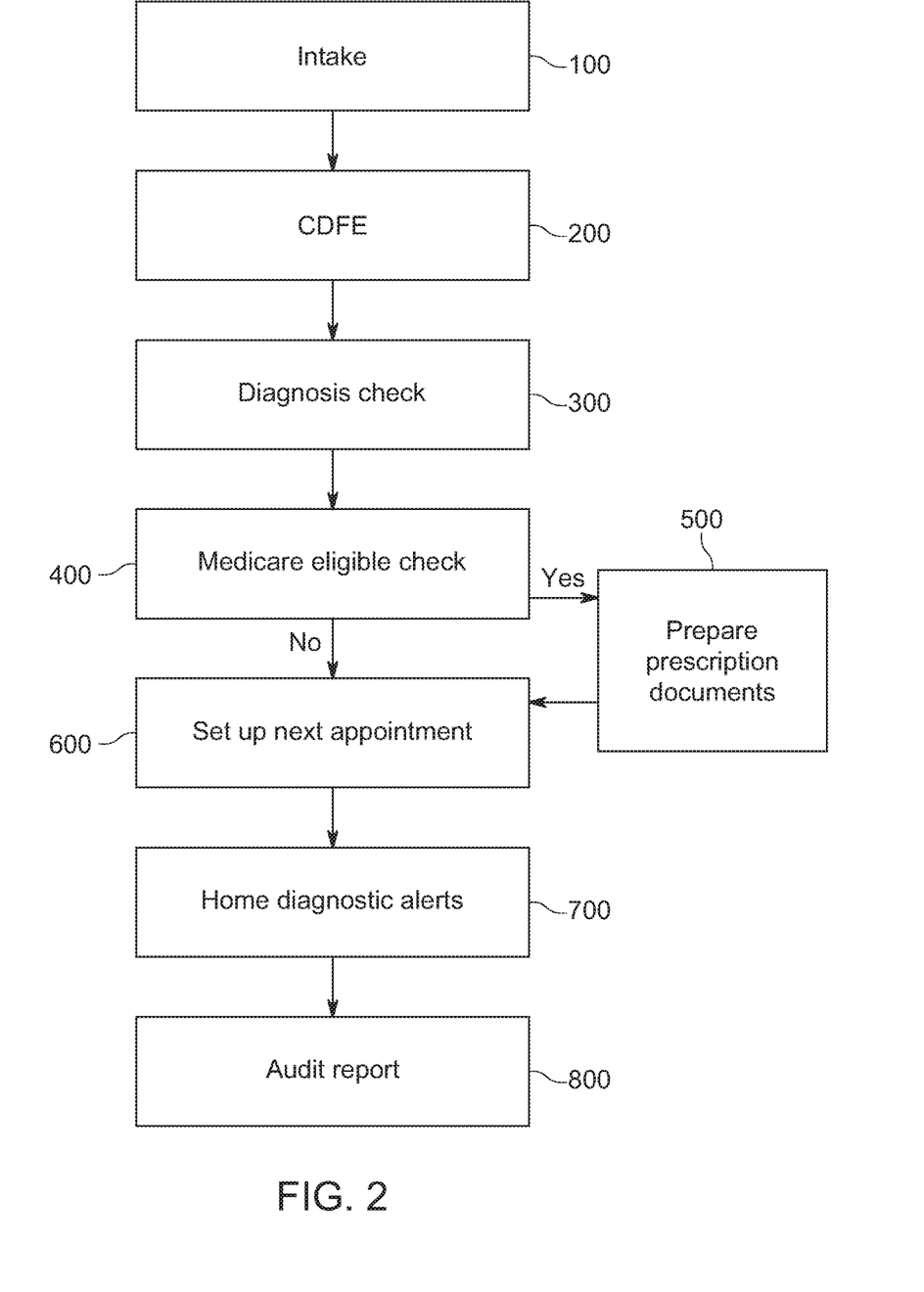
FIG. 2 is an overview flow diagram for the operation of the present system, in accordance with one embodiment.
Figure 3A:
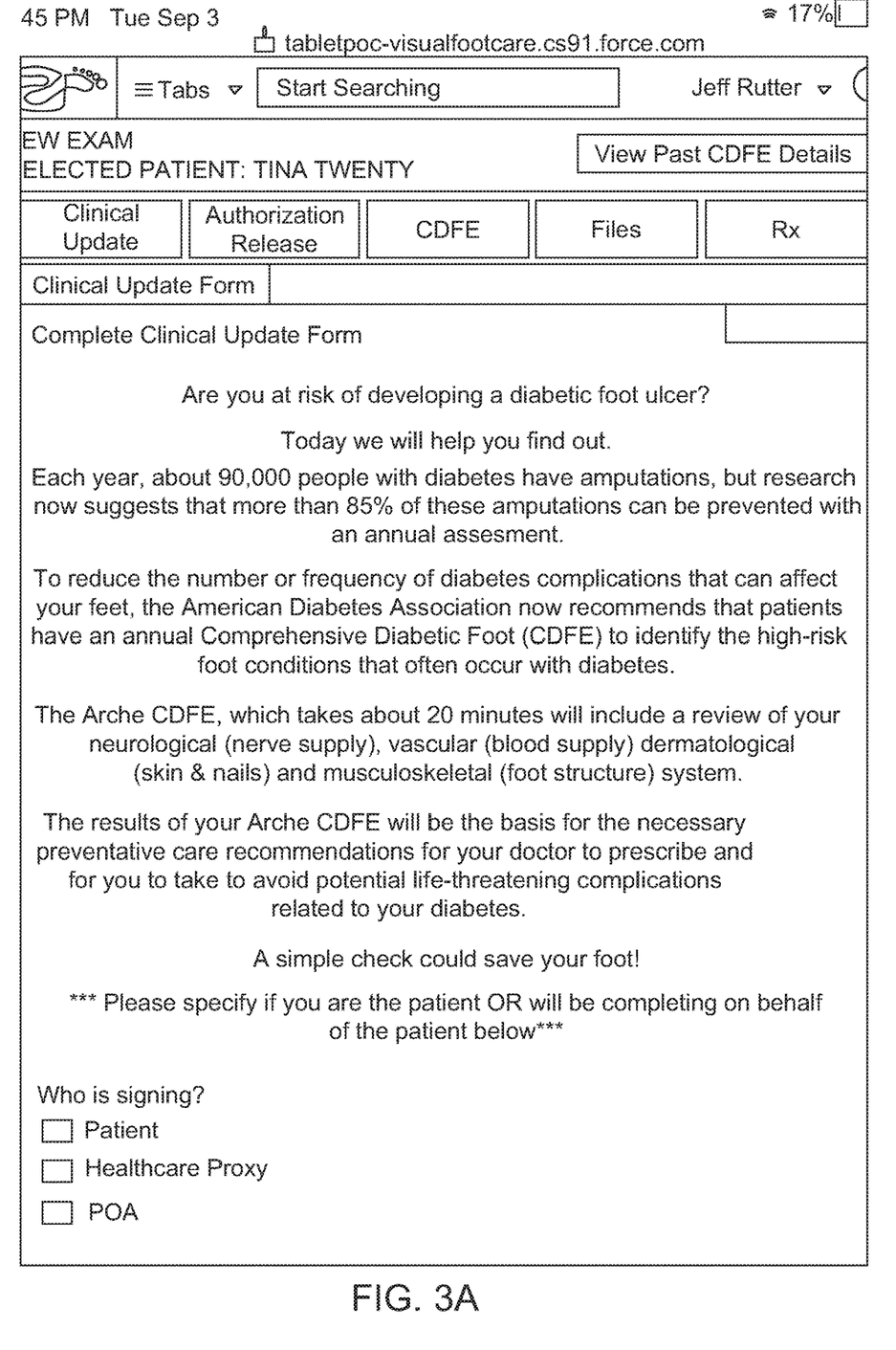
FIGS. 3A-3D illustrate exemplary clinical update form screen shots for new patients, in accordance with one embodiment.
Figure 3B:
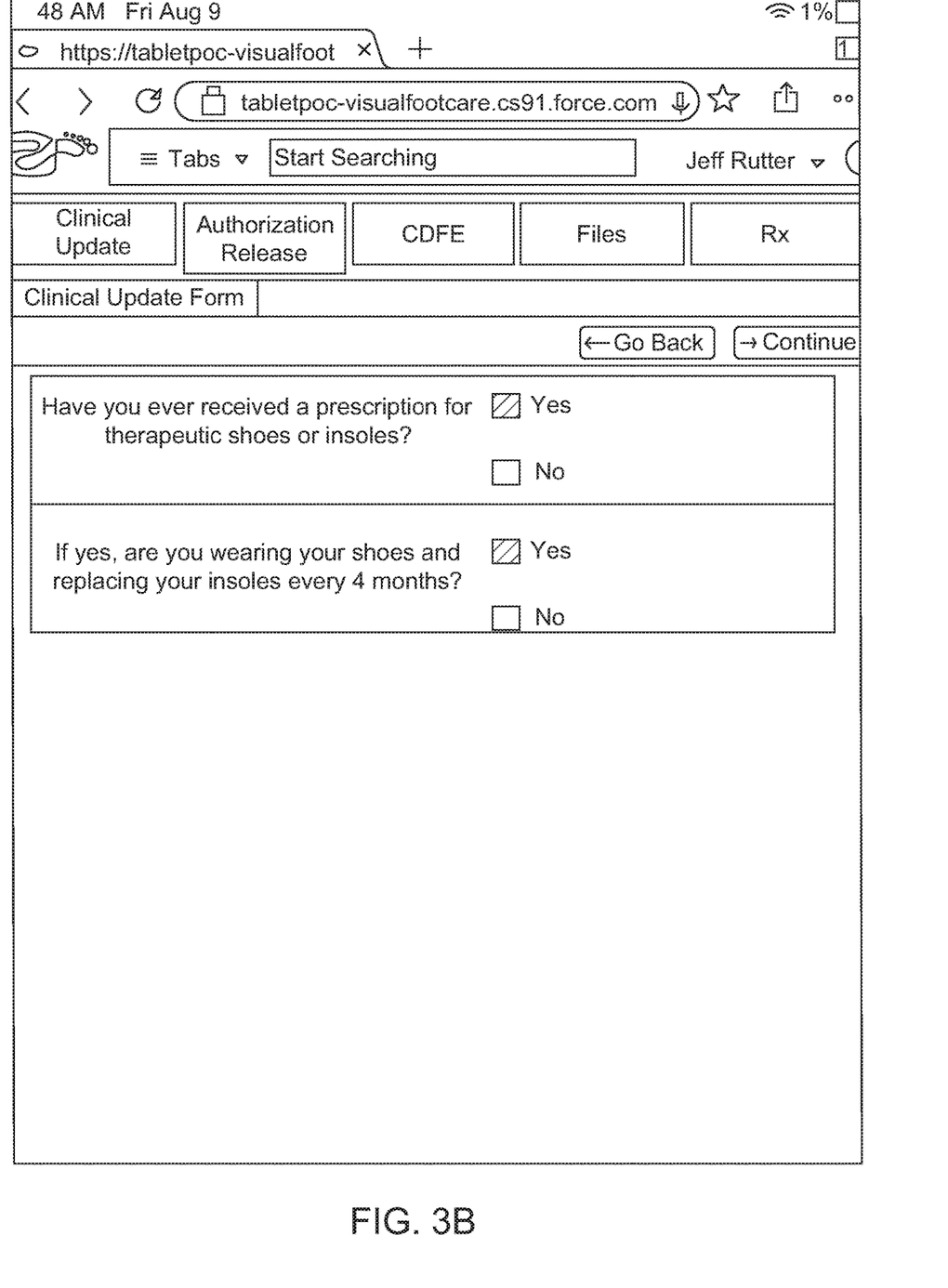
Figure 3C:
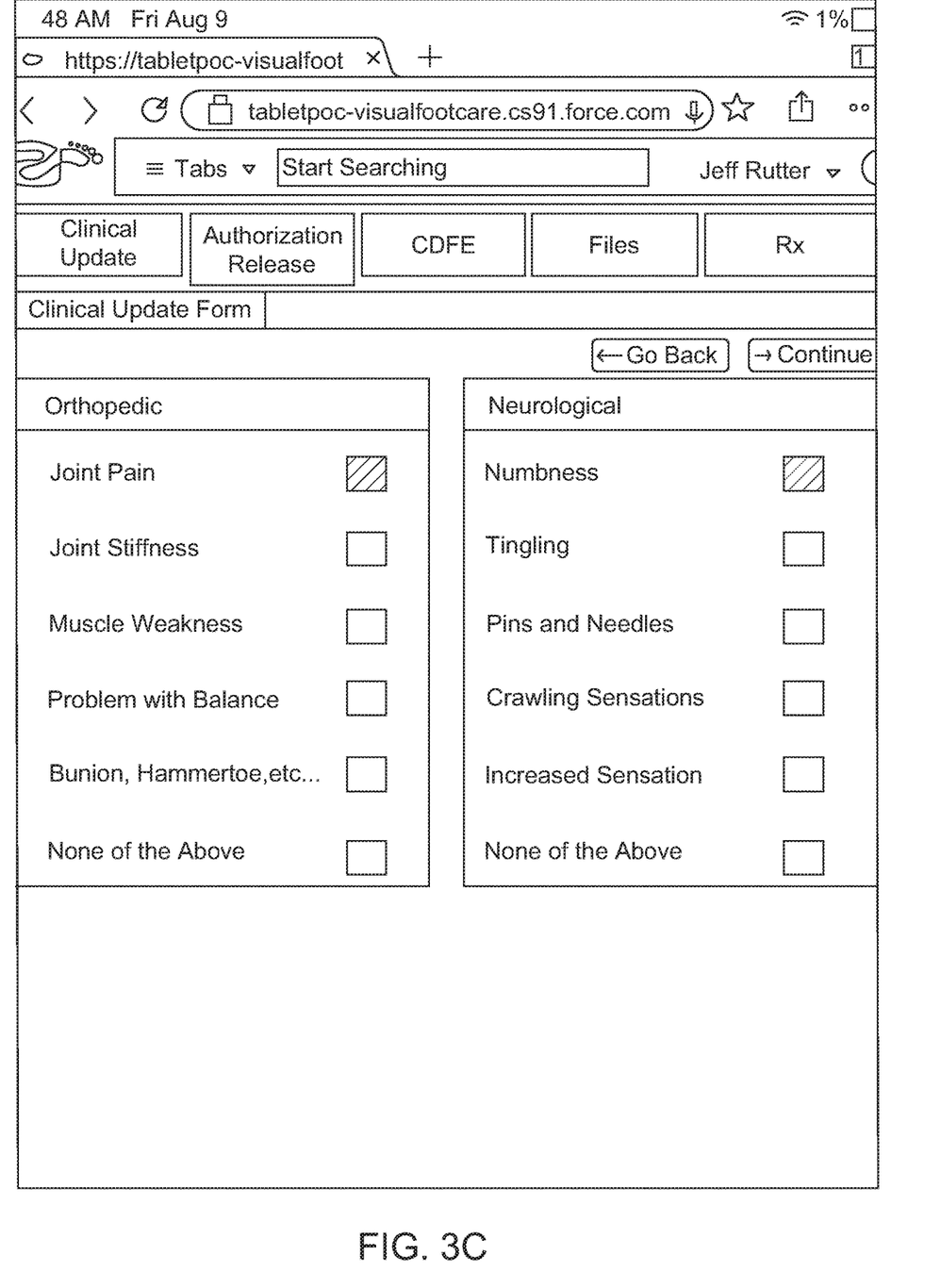
Figure 3D:
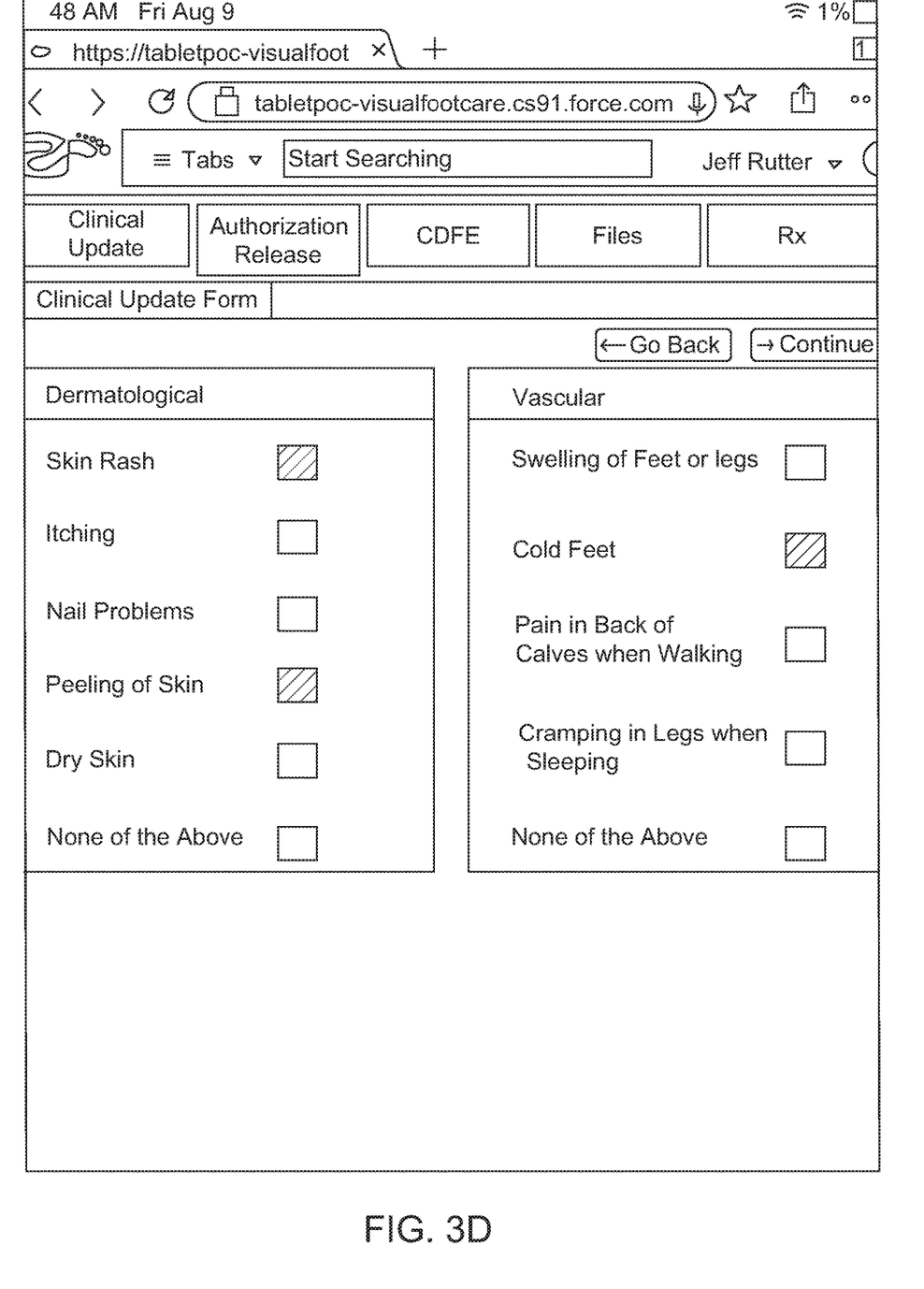

In another embodiment, FIG. 2 shows an overview of the operation of system 10 as implemented for example, by a doctor managing a plurality of patients with diabetic foot care issues. Such a flow diagram includes, but is not limited to, the following described stages, starting with the intake of a patient at step 100. Thereafter, at step 200 the doctor conducts a comprehensive diabetic foot examination, with the input of such results into patient data 22 of system 10 and makes a risk level diagnosis of the patient.

During this process at step 300, system 10, using such diagnosis information, runs an analysis against the collected data and the doctor diagnosis to ensure compliance with accepted practices for patient risk pools. For example, as described in more detail below, patients exhibiting certain characteristics are eligible to categorization in particular risk pools described for example in the table in the above background section (e.g. risk pool 0, 1, 2, or 3—low to high). At step 300, system 10 checks the various patient test data and exam input results by the doctor against the assessed risk stratification level to ensure that it is a correct assignment of risk stratification. If a possible error is detected (e.g. risk pool diagnosis does not match the conditions of the patient as entered during the exam) then an alert is presented to the doctor to force the doctor to double check the examination results and to ensure that the risk pool assessment is correct.

Thereafter, at step 400, once steps 200 and 300 are complete, the examination results from step 200 are run against the clinical risk indicators used by Medicare stored in directory 26 of system 10 to detect if the patient may be eligible for therapeutic footwear and insoles. In other words at this step the examination data collected at step 200 that was first checked against the risk pool diagnosis entered (at step 300) is also simultaneously run against the clinical risk indicator data used by Medicare to separately indicate if the patient is eligible for insurance covered therapeutic footwear and insoles.

Assuming the answer above is yes, at step 500, system 10 incudes a sub-routine process to obtain the required documentation for an accepted prescription for such footwear/insoles. For example, Medicare requires documentation of an examination that meets the required prescription criteria as well as signatures from the primary care physician or endocrinologist treating the diabetic patient. At step 500, the system prepares such paperwork for the patient and doctor and sends messages/facsimiles to obtain the required signatures.

At step 600, once the exam is done, and any prescriptions may be ordered, the doctor, based on their diagnosis can set up follow up appointments at the prescribed time (e.g. lower risk patients once a year, high risk patients in 3 months or less, etc. . . . )

Next at step 700, a patient may be provided with at home test equipment including but not limited to moisture testing, plantar foot temperature testing, and/or photograph images of the bottom of the foot. Such data may be collected on a patient at home application (e.g. phone app, desktop app etc. . . . ) and sent to system 10 to be stored in patient data 22. The data collection application may be further be implemented with alerts. For example if a home test detects a hot spot on the plantar foot temperature analysis, the data, when sent will include an alert that will be forwarded to the doctor to contact the patient, prior to the next ordinary visit, to discuss the issue by phone and potentially treat the issue at the office if needed.

Finally, at step 800, in the event of an audit of the doctor, either by Medicare or any other involved insurance or third-party payor, system 10, keeps records of patient interactions from intake, examination, diagnosis, and prescriptions up to and including all follow up appointments. In the instance of an audit of the doctor, system 10 is configured to prepare audit reports that can fully document patient diagnosis, and further fully documents the associated prescriptions and that such prescriptions meet the payors' requirements, without the need of the doctor to manually go back and recreate and synchronize such data.

The above represents an exemplary flow of the patient management by system 10, but it is understood that additional steps may be added, or some steps removed (in some cases), as desired by the patient and/or doctor.

The following descriptions provide further details of the above described steps.

Regarding step 100, the step of patient intake includes but is not limited to completion of a Clinical Update Form to capture any new complaints and symptoms, completion of a Release of Information Form that includes confirmation of the patient's physician managing their diabetes (PCP or endocrinologist) and assignment of power of attorney or healthcare proxy if necessary. Other data collected may or may not include the patients name, age, contact information, prior medical history forms filled out by the patient as well as importing electronic medical data from other doctors including the patients' diabetes history, prior diagnoses, image files etc. . . . . See for example FIGS. 3A-3D showing exemplary clinical update form screen shots.

Regarding step 200, for each patient managed in system 10, a Comprehensive Diabetic Foot Examination (CDFE) is conducted. The Examination includes a series of measurements and tests, observations, as well as questions/answers thoroughly conducted by the doctor and their staff.

Patient tests may include, but are not limited to, monofilament testing to evaluate sensory perception and neuropathy, VibraTip to assess vibratory sensation and neuropathy, DermaStat to measure skin moisture index, IR Stat to measure temperature discrepancies between feet, Pressure Stat to evaluate areas of focal pressure on the plantar surface of the feet and a Brannock device to measure potential change in foot size. Patient observations may include but are not limited to measurement of pulses, evaluation of skin for signs of peripheral vascular disease and visual inspection for deformities, inflammation, ulceration or other wounds. The patient may respond as to whether or not they feel the monofilament or vibration, as part of a diagnostic exam. The patient can also tell their doctor about any symptoms they have, which could include complaints of pain, tingling, numbness, etc. It is understood that there may be some overlap between the data collected at this step 200 and that collected at step 100 in the clinical update form. For example, patients may be asked if they have had a previous ulcer and if they have had therapeutic footwear and insoles in the past and whether or not they are wearing them, both on the intake form and during the CDFE.

Figure 4:
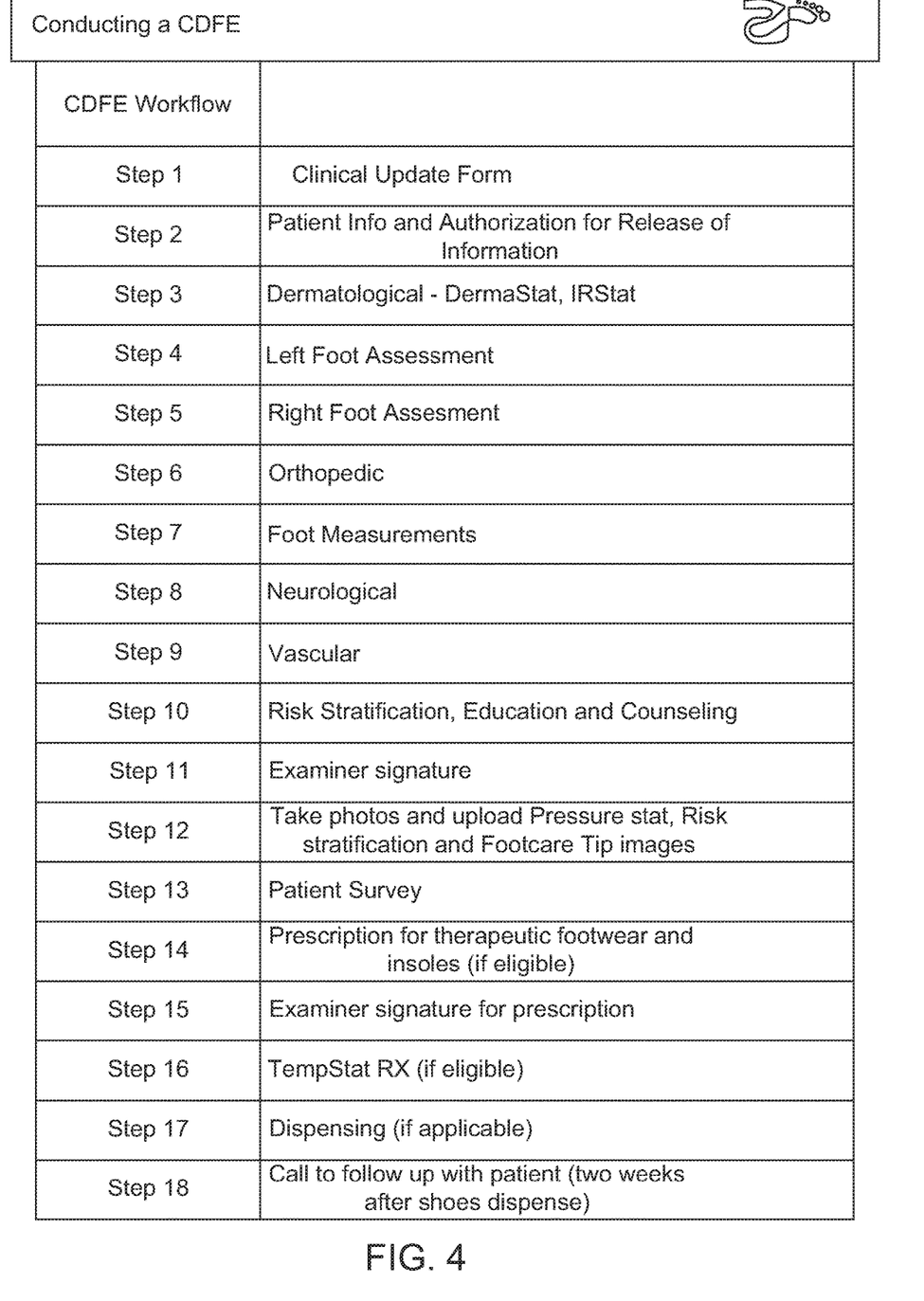
FIG. 4 illustrates an exemplary flow for reception of clinical update data and comprehensive diabetic foot exam data, in accordance with one embodiment.

FIG. 4 shows an exemplary set of steps for the CDFE, particularly steps 2-13, that include the various types of examinations/observations made by the doctor when evaluating the foot to make the appropriate risk assessment. Such assessments may include but are not limited to those that are used in other foot exams to determine amputation risk in diabetic foot patients, such as: dermatological tests; physical foot assessments (ulcers, dry skin, redness, swelling, bunions, hammer/claw toe, amputations, ulcers, etc. . . . ); orthopedic range of motion tests; foot size measurements; neurological tests; vascular tests; and any other related tests that could help assess diabetic foot risk.

Regarding step 300, the doctor, after taking in the above information during the CDFE at step 200 makes an assessment for a risk pool associated with the patients (apart from any direct diagnoses such as identification of an active ulcer). The risk pool assessment may be based on the following table, similar to that shown above in the background section . . . .

TABLE 2

International working Group on the Diabetic Foot (IWGDF) Risk Classification System

| Level | Status | Interventions |
|---|---|---|
| 0 | Diabetes without sensory neuropathy | Annual Arche CDFE with Patient Education |
| 1 | Sensory Neuropathy only | Annual Arche CDFE with patient education<br>61 day @risk foot care<br>Footwear and insole Rx<br>Daily surveillance with TempStat |
| 2 | Sensory neuropathy with PVD and/or deformity | Annual Arche CDFE with patient education |

TABLE 2-continued

International working Group on the Diabetic Foot (IWGDF) Risk Classification System

| Level | Status | Interventions |
|---|---|---|
| | without previous history of wound or amputation | 61 day @risk foot care<br>Footwear and insole Rx<br>Daily surveillance with TempStat |
| 3 | previous wound or amputation | Annual Arche CDFE with patient education<br>61 day @risk foot care<br>Footwear and insole Rx<br>Daily surveillance with TempStat |

Once an assessment is selected by the doctor, they enter it into patient data 22 of system 10. However, system 10 is configured to apply data contained in diagnosis check database 24 to confirm that the assessment meets the ordinary requirements for that risk pool.

For example, each of the various data points in step 200 during the CDFE pertain to some aspect of reaching a final assessment in step 300 in the above table. One example is a "current ulcer" which would require an assessment of "3" with associated two month follow up visit schedules and other preventive measures. Additionally, the assessment of risk pool "3" would result in being eligible for prescription footwear or inserts as explained below.

However, in some cases, a doctor may make and enter certain observations in step 200 (e.g. active ulcer on a toe) but then accidentally assesses the patient at risk level "1." In such instances, the system will cross check all of the various input factors that should lead to a particular risk pool assessment against the actual input factors entered during the CDFE and confirm that the final risk pool diagnosis entered by the doctor is an acceptable number. If not, an alert will prompt the doctor to re-check the CDFE entries and reconfirm both the assessment and the CDFE entries. In the above example the doctor would be alerted to the fact that a risk pool assessment of "1" is not compatible with a simultaneous entry during the CDFE of an active ulcer, and they would be prompted to correct one or the other (either the "1" was wrong or the "active ulcer" entry was wrong.

Such an arrangement prevents mis-assessments of the risk pool but also ensures that future activity and prescriptions based on the assessment are properly accounted for and supported in the case of any future audits by third-party payors.

Regarding step 400 once a confirmed risk pool assessment is made, the present system 10 further runs the results of the CDFE from step 200 against a separate set of diagnostic data stored in Medicare data 26 of database 20. It is noted that a patient is eligible for prescription footwear/insoles if they meet certain Medicare clinical risk indicators. These risk indicators overlap with, but do not match, the same factors that result in the risk pool assessment categories. As such, in order to qualify for prescription coverage under Medicare (and for other third-party payor insurance plans adopting similar risk indicators), the CDFE needs to be run against such indicators, separate from the risk pool diagnosis.

For example, patients diagnosed to be in risk pools "2" or "3" will also always meet the clinical risk indicator requirements for Medicare eligibility for footwear/insole reimbursement. However, for patients with risk pool assessment in the "0" and "1" level they may be eligible for a prescription if they have one or more of the following specific indicators called for in the clinical risk indicators of Medicare and also potentially recorded in the CDFE:

Foot deformity of either foot, with or without neuropathy
Poor circulation as indicated by non-palpable Dorsalis Pedis or
Posterior Tibial pulses and/or capillary refill time of >3 seconds and a pre-ulcerative callus.

Other examples of overlap between lower risk but therapeutic footwear and insole eligibility may exist now or in the future depending on changes in the relevant criteria.

As such, once a level 2 or 3 assessment is reached or after system 10 identifies a CDFE data point that meets the clinical risk indicator requirements (even if patient is risk level "0" or "1") then system 10 alerts the doctor to begin a prescription ordering routine described below in relation to step 500. If not eligible the management routine skips to step 600.

Figure 5:
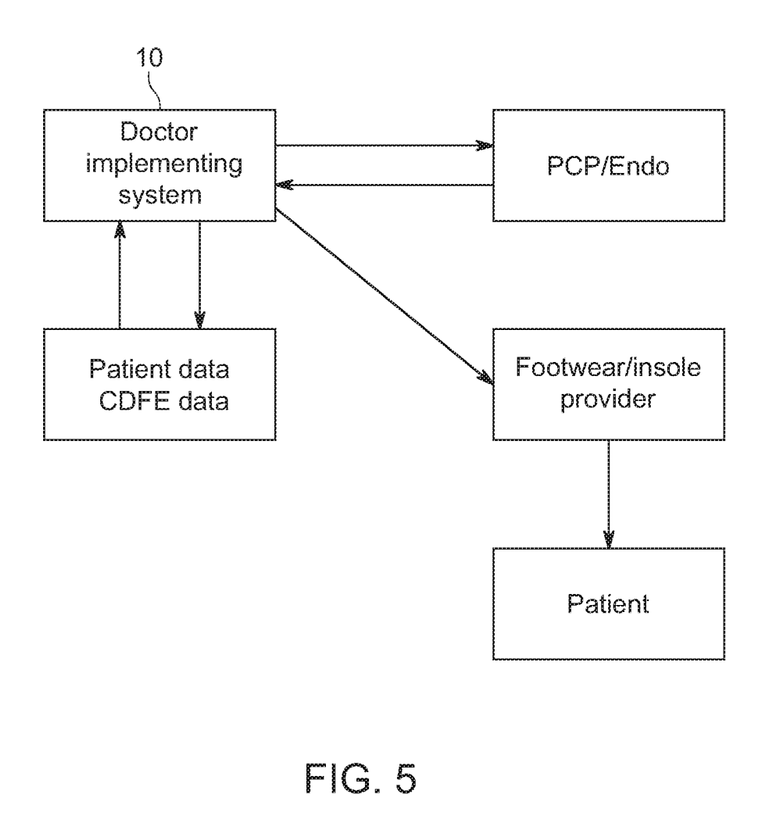
FIG. 5 illustrates a prescription fulfillment routine, in accordance with one embodiment.

Regarding step 500, in one embodiment, assuming a patient is eligible for footwear/insoles, system 10, such as processor 12 generates the required forms for completing a valid Medicare compliant prescription/remuneration transaction. As shown in FIG. 5, such a process may include but is not limited to pre-populating forms using the patient intake information (step 100) as well as information collected during the CDFE (step 200). System also connects with the patient's primary care physician to obtain the required confirmation signatures required to secure the prescription. This may be transmitted by facsimile, e-mail and the like and, after the signed copy is received, it is stored with the patient records.

Once the prescription documentation is completed, system 10 may send the required order form to a third-party vendor to have the footwear/insoles delivered to the doctor's office to be dispensed, along with the commensurate management, storage and/or delivery of the required paperwork. Such an arrangement helps automate the process for ordering using the already prepared CDFE data and provides solid records for a potential audit as described in more detail below.

After the prescription filling process step 500 (assuming there is one), system 10 may also provide automated and/or semi-automated scheduling of future appointments for the patient at step 600. Generally, a patient is scheduled for an annual CDFE. If they do not have that appointment within 14 months of the last CDFE, system 10 may in some cases be able to send automated appointment reminders, if they have opted into that service. System 10 may also track missed/overdue appointments in the patient data and also in their own practice metrics.

In other cases, where a patient is assessed at a higher risk level such as level 1, 2, or 3, they may qualify for a 61 day at-risk follow up foot care appointment. System 10 may be arranged to automatically highlight the risk assessment level previously determined to ensure that the appointment agent makes such a follow up decision.

Figure 6:
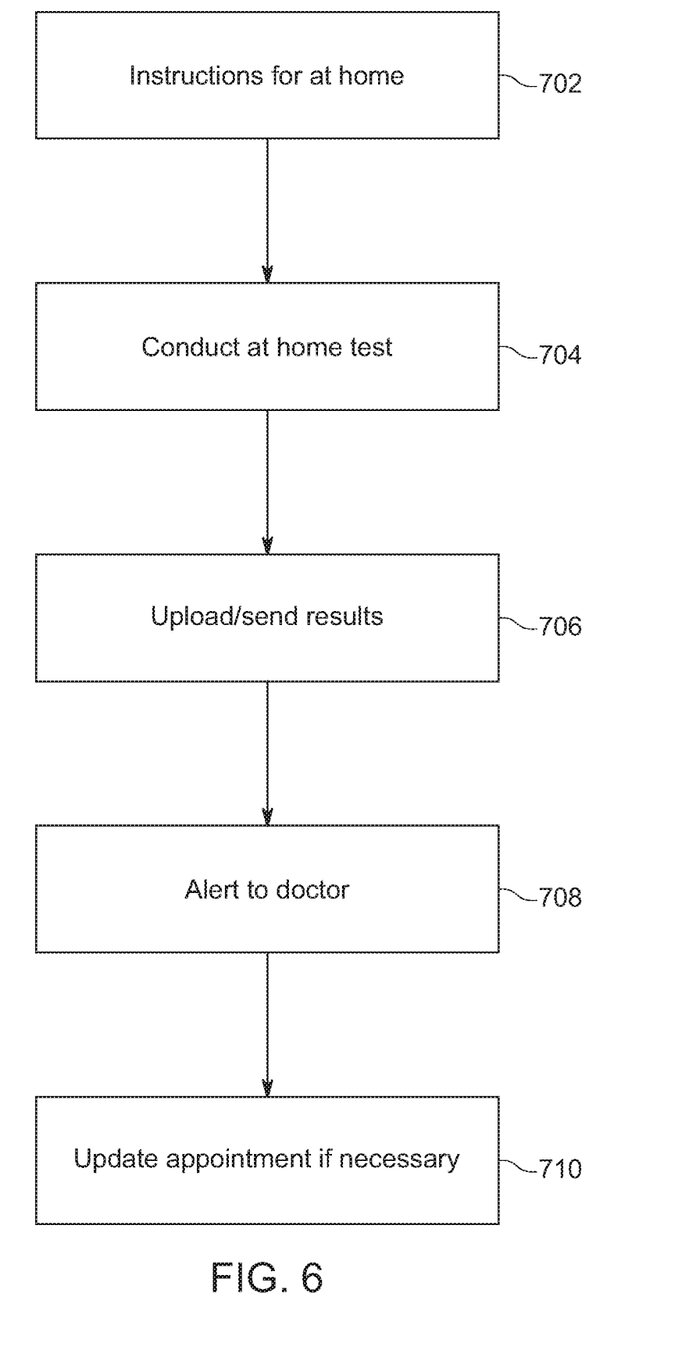
FIG. 6 illustrates an at-home examination, in accordance with one embodiment.

Once a patient leaves the doctor FIG. 6 outlines the various possible subroutine steps for step 700 relating to at home monitoring by the patient. Upon completion of the CDFE and appointment, and upon the risk level assessment, the patient can be given instructions at stage 702 for various at home testing arrangements. At home testing kits may include but are not limited to: TempStat™ or InSight™ (e.g. for at home measurement of plantar foot temperature, and including possible images of the bottom of the foot); DermaStat™ (e.g. for at home measurement of the skin moisture on the foot); PressureStat™ (e.g. pressure testing for at home foot check—areas of high pressure being denoted by a darker area on the footprint image are at greater risk for ulceration); and VibraTip™ (e.g. to assess vibratory sensory perception (to detect neuropathy—loss of feeling).

At subroutine 704 after the user is instructed on the operation of the at home testing equipment, in one embodiment, a patient may download a program or app (application) called VeriSole™ that will allow them to upload their results from the at home testing device (either manually or automated/Bluetooth etc. . . . ). For example, in the case of at home temperature monitoring, a user may either input their temperature readings/detected hot spots or they may have them directly transferred from their at home temperature measuring device (e.g. TempStat™ or InSight™ device), possibly with accompanying images to the monitoring application on their smart phone device.

Next, at step 706 such results are transmitted to system 10 for both storage in their associated patient data 22 in database 20. In other embodiments the collected at home test results may be transmitted manually, by phone, or fax or other such methods as required. At step 708 in one embodiment, once at home test data is in system 10, an alert is sent to the doctor to make sure they review. In another embodiment, certain data may be subject to AI (artificial intelligence) analysis to help this process. This may include some automated pre-screening of the test data for troublesome issues. For example, it is possible system 10 may review TempStat or InSight temperature data and if an area of elevated temperature exceeds a certain threshold, system 10 may, in addition to alerting the doctor the presence of the collected results, may also further indicate a possible problem area so that the doctor does not overlook the issue. Similarly, changes in Skin Moisture Index indicating progression to sudomotor dysfunction can be analyzed and used to alert the physician managing the patient. Alternatively, AI detected problems may receive differentiated type of "high" alert rather than a normal alert.

Finally, at step 710 after the doctor has reviewed the patient's home monitoring results, they may request a change in the appointment schedule. For example, a patient with a CDFE assessment score of 1 may utilize a home test such a temperature test device. Ordinarily, a risk assessment of 1 at the CDFE would mean 1-year between appointments. However, if the patient sends a home monitoring result to the doctor with an elevated temperature location indicative of a possible infection or ulceration, the doctor may adjust the appointment schedule previously set in system 10 to something more immediate.

Figure 7:
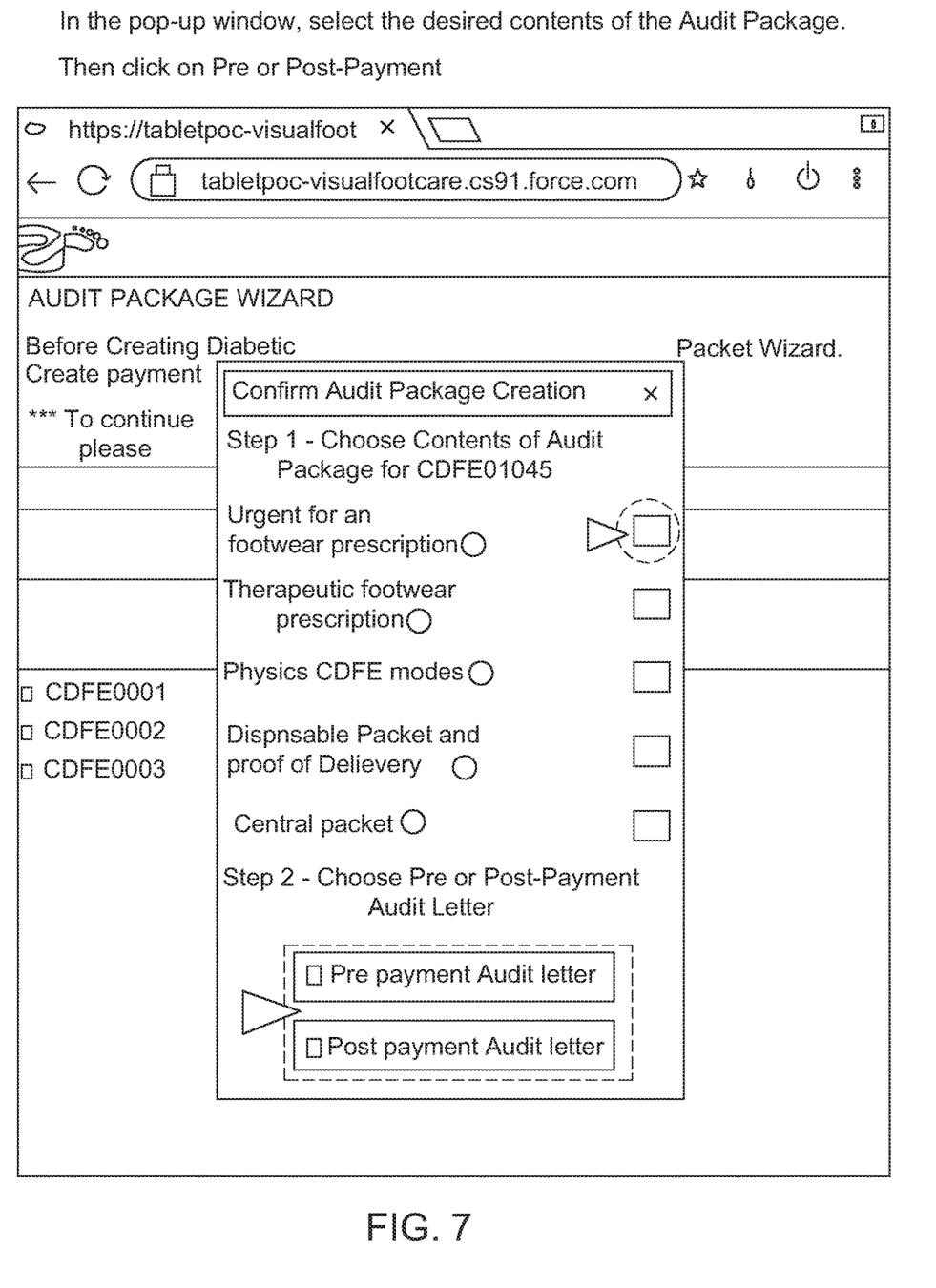
FIG. 7 illustrates an exemplary audit selection page, in accordance with one embodiment.

In another embodiment of the present invention as shown in FIG. 7, system 10 is configured, as outlined above to continuously store data related to patient intake information (step 100), CDFE results (step 200), Medicare footwear/insole eligibility tests (step 400), prescription acquisition (step 500) and at home diagnostics (step 700). Medicare and other third-party insurance providers often request audits of certain doctors offices to ensure compliance for various services and reimbursements to ensure compliance with the applicable standards. However, as noted above in the background, such disparate processes often relate to disparate collection and storage of the related data making audit compliance very difficult.

The present application, storing all relevant data for the CDFE process, start to finish, in a single database 20, system 10 is able to provide an easy and efficient manner for producing an audit report of an entire population of the patient pool for the doctor's offices.

Figure 8:
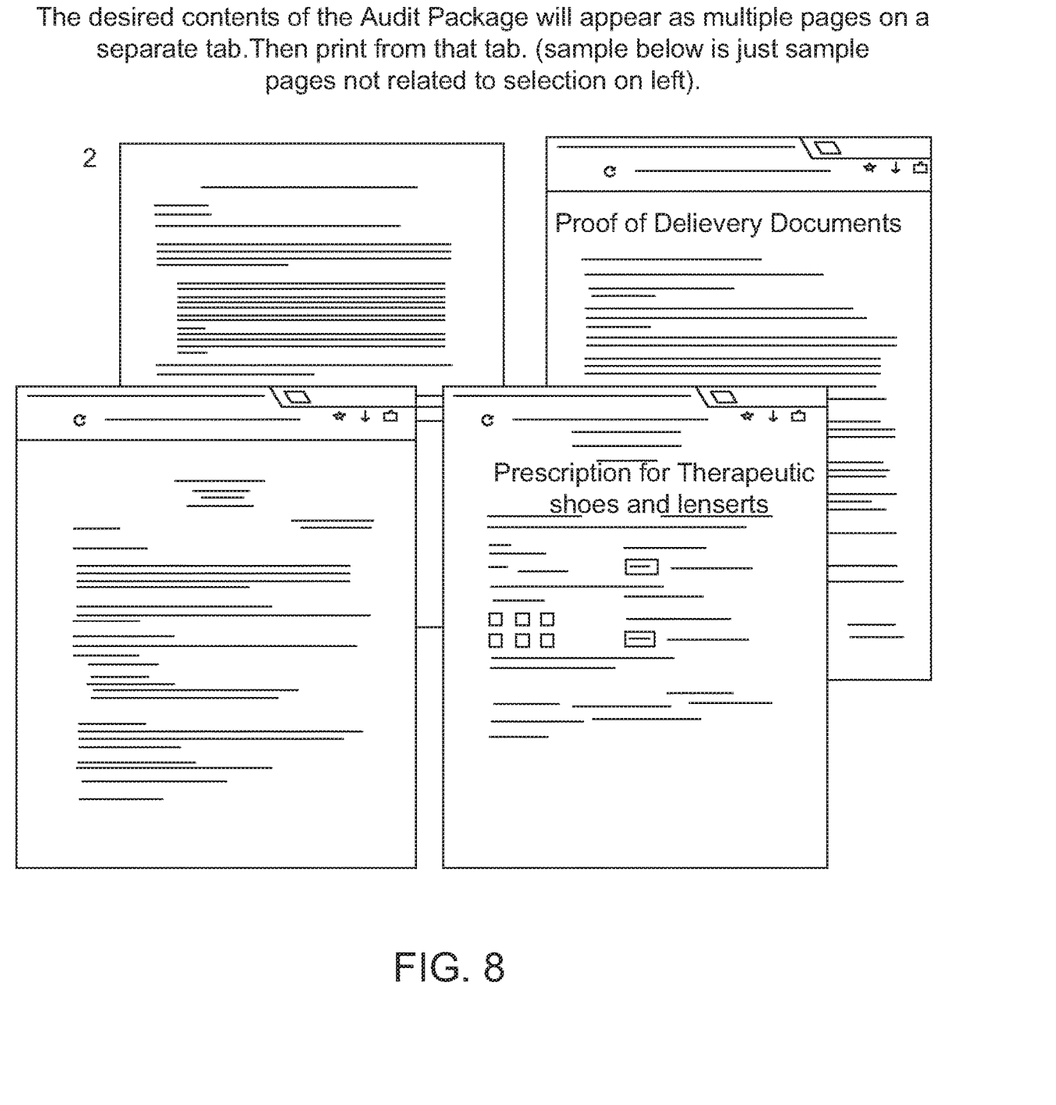
FIG. 8 illustrates an exemplary audit form, in accordance with one embodiment.

To this extent as shown in FIG. 7 a doctor need only access system 10 and select an audit report parameter from the available parameters from the CDFE and, as shown in FIG. 8, an audit report 800 is issued as required for compliance.

While only certain features of the invention have been illustrated and described herein, many modifications, substitutions, changes or equivalents will now occur to those skilled in the art. It is therefore, to be understood that this application is intended to cover all such modifications and changes that fall within the true spirit of the invention.

The invention claimed is:

1. A system for managing diabetic foot care patients, said system comprising:
   a communication interface for transmitting diagnostic forms to a doctor device and receiving input from said doctor device;
   a processor for managing said transmissions and received input; and
   a database for storing said diagnostic forms and said received input, as well as pre-stored risk assessment guidelines;
   wherein said system is configured to transmit said diagnostic forms to a doctor device for guiding a comprehensive foot exam, said system further configured to accept doctor input including at least a first data set including foot examination details and a second set of data being a doctor assessed risk pool assessment based on a four-tier system;
   wherein said system is configured to store a third set of data including a table correlating said foot examination details to a pre-set risk pool assessment in the form of said four-tier system, said foot examination details including but not limited to: no sensory neuropathy, sensory neuropathy only, sensory neuropathy with PVD (Peripheral Vascular Disease) and/or visible physical deformity, and visible ulcer and/or past amputation,
   wherein said system is configured to compare said at least a plurality of foot examination details of said first data set against said foot examination details from the pre-stored risk assessment guidelines from said third data set and confirm or reject said doctor assessed risk pool assessment input by said doctor in said second data set if said risk pool assessment in said second data set is or is not congruent between said first data set and said third data set with requirements contained in said foot examination details to a pre-set risk pool assessment,
   wherein said system is further configured to store an independent fourth set of data including a separate listing of foot examination details, independent of foot examination details to a pre-set risk pool assessment in the form of said four-tier system in said third set of data, that separately meet a predetermined threshold for a third-party insurance coverage to issue covered orthotics to said diabetic foot care patients, and
   wherein if said system determines that first data set including foot examination details matches the criteria from said separate listing of foot examination details of said independent fourth set of data, said system generates a report for said third-party insurance coverage to issue covered orthotics to said diabetic foot care patients.

2. The system as claimed in claim 1, wherein said system is configured to intake a store patient intake questionnaire, prior to receiving said foot examination details.

3. The system as claimed in claim 1, wherein said comprehensive foot exam includes examination details selected from the group consisting of: skin moisture results, temperature results, plantar pressure results, protective sensation and vibratory sensitivity results, visual observations, vascular assessments, foot size measurements, accounting for ulcers.

4. The system as claimed in claim 1, wherein said foot examination details in said first set of data must include elements from said four-tier system commensurate with said risk pool assessment from said third set of data, or said system rejects said doctor applied risk pool assessment of said second set of data.

5. The system as claimed in claim 1, wherein said system is further configured to receive input from at least one at home testing device, operated by said patient.

6. The system as claimed in claim 5, wherein if said input from said at home testing device indicates a medical issue with the patient's foot, said system is configured to automatically generate an alert to said doctor.

\* \* \* \* \*